US012678423B2

(12) United States Patent
Okano et al.

(10) Patent No.: US 12,678,423 B2
(45) Date of Patent: Jul. 14, 2026

(54) THERAPEUTIC AGENT FOR AMYOTROPHIC LATERAL SCLEROSIS AND COMPOSITION FOR TREATMENT

(71) Applicant: KEIO UNIVERSITY, Tokyo (JP)

(72) Inventors: Hideyuki Okano, Tokyo (JP); Koki Fujimori, Tokyo (JP); Hironobu Okuno, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 726 days.

(21) Appl. No.: 16/328,636

(22) PCT Filed: Aug. 29, 2017

(86) PCT No.: PCT/JP2017/030899

§ 371 (c)(1),
(2) Date: Jun. 20, 2019

(87) PCT Pub. No.: WO2018/043476

PCT Pub. Date: Mar. 8, 2018

(65) Prior Publication Data

US 2021/0113525 A1 Apr. 22, 2021

(30) Foreign Application Priority Data

Sep. 2, 2016 (JP) ................................ 2016-172255

(51) Int. Cl.
*A61K 31/404* (2006.01)
*A61P 25/00* (2006.01)

(52) U.S. Cl.
CPC ............ *A61K 31/404* (2013.01); *A61P 25/00* (2018.01)

(58) Field of Classification Search
None
See application file for complete search history.

(56) References Cited

U.S. PATENT DOCUMENTS

2013/0274235 A1* 10/2013 Isacson .................. G01N 33/74
514/180

FOREIGN PATENT DOCUMENTS

| | | | |
|---|---|---|---|
| JP | 2014196268 | * | 10/2014 |
| WO | 2012/048330 | A2 | 4/2012 |

OTHER PUBLICATIONS

Dagvajantsan et al., Up-Regulation of Insulin-Like Growth Factor-II Receptor in Reactive Astrocytes in the Spinal Cord of Amyotrophic Lateral Sclerosis Transgenic Rats. The Tohoku Journal of Experimental Medicine, 2008, 214, 303-310.*

(Continued)

*Primary Examiner* — Po-Chih Chen
(74) *Attorney, Agent, or Firm* — LATHROP GPM LLP; Brian C. Trinque; Tanya S. D'Souza

(57) ABSTRACT

A therapeutic agent for amyotrophic lateral sclerosis including a compound represented by Formula (1) [in Formula (1), $R^1$ each independently represents an alkyl group having 1 to 6 carbon atoms or 4-hydroxyphenethyl group, and n represents an integer of 1 to 3], a pharmaceutically acceptable salt thereof, or a solvate thereof, as an effective ingredient.

(1)

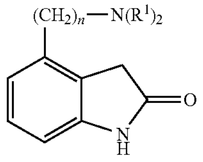

6 Claims, 13 Drawing Sheets

(56) References Cited

OTHER PUBLICATIONS

Corrado et al., Mutation of FUS gene in sporadic amyotrophic lateral sclerosis. Journal of Medical Genetics, 2010, 47, p. 190-194.*
Machine-generated English translation of Foreign Patent No. JP2014196268, published on Oct. 16, 2014.*
Ichiyanagi, N. et al. (2016) "Establishment of In Vitro FUS—Associated Familial Amyotrophic Lateral Sclerosis Model Using Human Induced Pluripotent Stem Cells," Stem Cell Reports, vol. 6, pp. 496-510.
Julien, J. P., et al., (2006) "Transgenic mouse models of amyotrophic lateral sclerosis," Biochimica et Biophysica Acta, 1762(11-12):1013-1024.
Moser, J. M., et al., (2013) "The wobbler mouse, an ALS animal model," Mol. Genet. Genomics., 288(5-6):207-229.
Nagata, E. et al., (2016) "Bromocriptine Mesylate Attenuates Amyotrophic Lateral Sclerosis : A Phase 2a, Randomized, Double-Blind, Placebo-Controlled Research in Japanese Patients," PLoS ONE, vol. 11, No. 2, e0149509, pp. 1-16.
Van Den Bosch, L. et al. (2006) et al., "The role of excitotoxicity in the pathogenesis of amyotrophic lateral sclerosis," Biochim. Biophys. Acta, 1762(11-12):1068-1082.
International Search Report for PCT/JP2017/030899 dated Oct. 24, 2017.
Da Cruz et al., "Misfolded SOD1 is not a primary component of sporadic ALS", Acta Neuropathol, 2017, 134: 97-111.
Deng et al., "FUS-Immunoreactive Inclusions Are a Common Feature in Sporadic and Non-SOD1 Familial Amyotrophic Lateral Sclerosis", Ann Neurol., 2010, 67: 739-748.
Liu et al., "Lack of Evidence of Monomer/Misfolded Superoxide Dismutase-1 in Sporadic Amyotrophic Lateral Sclerosis", Ann Neurol., 2009, 66: 75-80.
Philips et al., "Rodent Models of Amyotrophic Lateral Sclerosis", Curr Protoc Pharmacol., Jun. 1, 2016, 69: 5.67.1-5.67.21.
Fujimori et al., "Modeling sporadic ALS in iPSC-derived motor neurons identifies a potential therapeutic agent", Nature Medicine, Oct. 2018, vol. 24, pp. 1579-1589.
Trotti et al., "SOD1 mutants linked to amyotropic lateral sclerosis selectively inactivate a glial glutamate transporter", Nature, May 1999, vol. 2, No. 5, pp. 427-433.

* cited by examiner

THERAPEUTIC AGENT FOR AMYOTROPHIC LATERAL SCLEROSIS AND COMPOSITION FOR TREATMENT

TECHNICAL FIELD

The present invention relates to a therapeutic agent for amyotrophic lateral sclerosis (ALS) and a composition for treatment of ALS. Priority is claimed on Japanese Patent Application No. 2016-172255, filed in Japan on Sep. 2, 2016, the content of which is incorporated herein by reference.

BACKGROUND ART

ALS is a neurodegenerative disease that causes severe muscle atrophy and muscle weakness and is a type of motor neuron disease. In ALS, lesions specific to motor neurons are observed and the disease progresses very rapidly with the average survival time after onset being several years. There is no effective treatment for ALS, and the development of a therapeutic agent as soon as possible is desired. Although the majority of cases of ALS are sporadic, 10% of patients have familial ALS and there are clear genetic factors involved.

A mutant mouse known as a wobbler mouse has been used as an ALS model since the mouse exhibits muscular atrophy of the forelimbs and facial muscles as the mouse grows and eventually exhibits muscular atrophy of the hind limbs (refer to, for example, NPL 1). However, it is known that the wobbler mutation is not observed in ALS patients.

In addition, SOD1 is known as one of the major causative genes of familial ALS, and a transgenic mouse into which mutant SOD1 has been introduced (NPL 2) is used in drug discovery research, but a drug exhibiting clear therapeutic effects is yet to be developed in clinical practice. Rather, the drugs selected using the SOD1-ALS model do not exhibit usefulness in actual ALS patients in the majority of cases, and there is currently a concern that the SOD1-ALS model may not be a functional model due to a disconnection between the SOD1-ALS model and actual clinical practice.

Thus, there was no good ALS model in the related art. This could be one reason why the development of therapeutic agents for ALS is not progressing.

Without being limited to ALS, there are intractable diseases for which no effective disease model exists. In recent years, disease research using iPS cells has been widely expected to produce disease models for these intractable diseases.

CITATION LIST

Non-Patent Literature

[NPL 1] Moser J. M., et al., The wobbler mouse, an ALS animal model., Mol. Genet. Genomics., 288 (5-6), 207-229, 2013.

[NPL 2] Julien J. P., Kriz J., Transgenic mouse models of amyotrophic lateral sclerosis, Biochimica et Biophysica Acta, 1762 (11-12), 1013-1024, 2006.

SUMMARY OF INVENTION

Technical Problem

An object of the present invention is to provide a therapeutic agent for ALS and a composition for treatment of ALS.

Solution to Problem

It is no exaggeration to say that disease-specific iPS cells are the only means for the in vitro reproduction of phenomena occurring in vivo in patients, especially in the nervous system. Using disease-specific iPS cells makes it possible to produce more accurate disease models than with existing cultured cells and disease model mice. In particular, regarding central nervous system diseases, using neurons differentiated from central nervous system disease-specific iPS cells makes it possible to select effective therapeutic drug candidates with high accuracy, not only clarifying the disease mechanism but also making the neurons into a more accurate disease model/efficacy evaluation model.

As will be described below in the Examples, the present inventors induced iPS cells derived from ALS patients to differentiate into motor neurons and administered a therapeutic agent for ALS, which will be described below, to motor neurons mirroring the ALS disease, to clarify that the ALS disease in the motor neurons improved. Accordingly, it is possible to treat ALS with the therapeutic agent for ALS to be described below.

In addition, the majority of ALS patients have sporadic ALS and, as described below in the Examples, the inventors found that the therapeutic agent for ALS to be described below improves the disease for both motor neurons mirroring the familial ALS disease and motor neurons mirroring the sporadic ALS disease. Accordingly, the therapeutic agent for ALS described below has a therapeutic effect on both familial ALS and sporadic ALS.

Since the therapeutic agent for ALS to be described below is a compound obtained by setting a phenotype found from analysis using a disease model using iPS cells derived from patients as an evaluation model and screening using a disease expressed in a transition period when the disease phenotype is observed as an indicator, rather than in a late stage close to cell death, the ALS therapeutic effect thereof is high.

The present invention includes the following aspects.

[1] A therapeutic agent for ALS, including a compound represented by Formula (1), a pharmaceutically acceptable salt thereof, or a solvate thereof, as an effective ingredient (1)

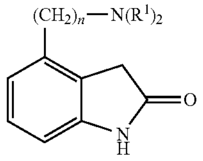

[in Formula (1), $R^1$ each independently represents an alkyl group having 1 to 6 carbon atoms or a 4-hydroxyphenethyl group, and n represents an integer of 1 to 3].

[2] The therapeutic agent for ALS according to [1], in which n in Formula (1) is 2.

[3] The therapeutic agent for ALS according to [1] or [2], in which IV in Formula (1) is an n-propyl group.

[4] The therapeutic agent for ALS according to any one of [1] to [3], in which the compound represented by Formula (1) is 4-(2-di-n-propylaminoethyl)-2(3H)-indole.

[5] The therapeutic agent for ALS according to any one of [1] to [4], in which the pharmaceutically acceptable salt of the compound represented by Formula (1) is 4-(2-di-n-propylaminoethyl)-2(3H)-indole hydrochloride.

[6] The therapeutic agent for ALS according to any one of [1] to [5], which has a therapeutic effect on both familial ALS and sporadic ALS.

[7] A composition for treatment of ALS including the therapeutic agent for ALS according to any one of [1] to [5] and a pharmaceutically acceptable carrier.

Advantageous Effects of Invention

According to the present invention, it is possible to provide a therapeutic agent for ALS and a composition for treatment of ALS.

BRIEF DESCRIPTION OF DRAWINGS

FIG. 14(*b*) is a graph enlarging the boxed portion of the graph of FIG. 14(*a*). FIG. 14(*c*) is a graph showing the neurite length of each motor neuron on days 50 and 62 from the induction of differentiation, as measured in Example I-9.

DESCRIPTION OF EMBODIMENTS

[Therapeutic Agent for ALS]

Figure 1:
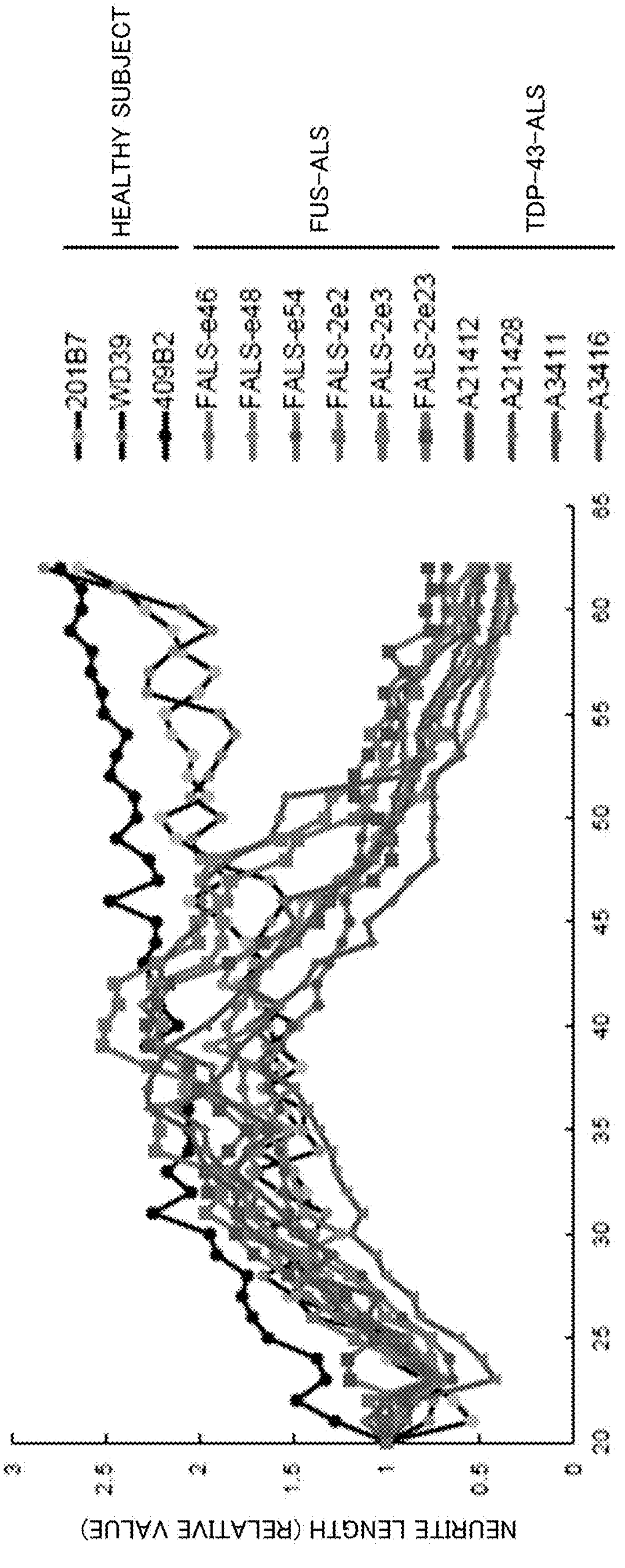
FIG. 1 is a graph showing the results of measuring changes over time in neurite length of motor neurons in Example I-2.

In one embodiment, the present invention provides a therapeutic agent for ALS containing a compound represented by Formula (1), a pharmaceutically acceptable salt thereof, or a solvate thereof, as an effective ingredient.

(1)

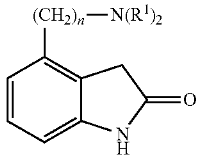

[In Formula (1), $R^1$ each independently represents an alkyl group having 1 to 6 carbon atoms or a 4-hydroxyphenethyl group, and n represents an integer of 1 to 3.]

Examples of familial ALS able to be treated with the therapeutic agent for ALS of the present embodiment include ALS having a mutation in the FUS gene, ALS having a mutation in the TAR DNA-binding protein 43 kDa (TDP-43) gene, and the like. In addition, as described below in the Examples, the therapeutic agent for ALS of the present embodiment has a therapeutic effect on both familial ALS and sporadic ALS.

In the therapeutic agent for ALS of the present embodiment, n in Formula (1) may be 1, 2, or 3.

In addition, in Formula (1), $R^1$ may be a linear, branched, or cyclic alkyl group having 1 to 6 carbon atoms and more specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, a cyclopentyl group, an n-hexyl group, a cyclohexyl group, and the like.

In the therapeutic agent for ALS of the present embodiment, the compound represented by Formula (1) may be 4-(2-di-n-propylaminoethyl)-2(3H)-indole. That is, the compound represented by Formula (1) may be ropinirole. The chemical formula of ropinirole is shown in Formula (2).

(2)

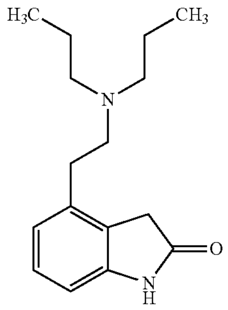

Ropinirole was developed as a drug for treating Parkinson's disease due to having a dopamine D2 receptor agonist activity in dopamine neurons. For this reason, the clinical trials thereof have already been completed and safety in a case of administration to living bodies has been sufficiently confirmed. Since ropinirole is an existing drug whose mechanism of action is clear, it is possible to rapidly develop a therapeutic agent for ALS by expanding the application thereof.

ALS is a disease caused by motor neuron disorder. That compounds which are D2 receptor agonists would show a therapeutic effect in degenerative diseases of motor neurons without D2 receptors was a surprising finding. It is also possible to anticipate finding clues regarding the disease mechanism of ALS and full clarification of the ALS disease from analysis of the mechanism of action of ropinirole.

The therapeutic agent for ALS of the present embodiment may be a salt of a compound represented by Formula (1), a solvate of a compound represented by Formula (1), or a solvate of a salt of a compound represented by Formula (1).

The salt is not particularly limited as long as the salt is a pharmaceutically acceptable salt, and examples thereof include inorganic acid salts such as hydrochloride, sulfate, hydrobromide, nitrate, and phosphate; organic acid salts such as acetate, mesylate, succinate, maleate, fumarate, citrate, and tartrate; alkali metal salts such as sodium salt and potassium salt; alkaline earth metal salts such as magnesium salt and calcium salt; metal salts such as aluminum salts and zinc salts; ammonium salts such as ammonium salts and tetramethylammonium salts; organic amine addition salts such as morpholine and piperidine; amino acid addition salts such as glycine, phenylalanine, lysine, aspartic acid, and glutamic acid, and the like.

In addition, the solvate of the compound represented by Formula (1) and the solvate of the salt of the compound represented by Formula (1) is not particularly limited as long as the solvates are pharmaceutically acceptable and examples thereof include hydrates, organic solvates, and the like.

The therapeutic agent for ALS of the present embodiment may be 4-(2-di-n-propylaminoethyl)-2(3H)-indole hydrochloride, that is, ropinirole hydrochloride.

[Composition for Treatment of ALS]

In one embodiment, the present invention provides a composition for treatment of ALS containing the therapeutic agent for ALS described above and a pharmaceutically acceptable carrier.

The composition for treatment of ALS of the present embodiment may be prepared as a pharmaceutical composition and, for example, is able to be administered orally in the form of tablets, capsules, elixirs, microcapsules, or the like, or parenterally in the form of an injection, a suppository, a skin external preparation, or the like. More specifically, examples of the skin external preparation include formulations such as ointments and patches.

As pharmaceutically acceptable carriers, it is possible to use pharmaceutically acceptable carriers usually used for preparing pharmaceutical compositions without particular limitation. More specific examples thereof include a binder such as hypromellose, dextrin, Macrogol 400, gelatin, corn starch, tragacanth gum, and gum arabic; excipients such as lactose hydrate, D-mannitol, starch, crystalline cellulose, and alginic acid; solvents for injections such as water, ethanol, and glycerin; adhesives such as rubber-based adhesives and silicone-based adhesives, and the like.

The composition for treatment of ALS may include additives. Examples of the additives include lubricants such as calcium stearate and magnesium stearate; sweeteners such as sucrose, lactose, saccharin, and maltitol; flavoring agents such as peppermint and akamono oil; stabilizers such as carmellose sodium, hydrogenated oil, light anhydrous silicic acid, povidone, glycerin fatty acid ester, benzyl alcohol, and phenol; buffering agents such as phosphate and sodium acetate; solubilizers such as benzyl benzoate and benzyl alcohol; coloring agents such as yellow ferric oxide, ferric oxide, black iron oxide, titanium oxide, and the like.

It is possible to prepare the composition for treatment of ALS by appropriately combining and mixing the therapeutic agent for ALS described above and the pharmaceutically acceptable carrier and additives described above in the form of a unit of a dose required for generally accepted pharmaceutical practice. In the composition for treatment of ALS of the present embodiment, one type of therapeutic agent for ALS may be used alone, or two or more types may be used in a mixture.

Generally, the appropriate daily dose of the composition for treatment of ALS is an amount including the lowest dose of the effective ingredient (therapeutic agent for ALS) effective for producing a therapeutic effect. The effective minimum dose described above is determined based on various factors including the activity of the active ingredient contained in the composition for treatment of ALS, the functional group modification which defines lipid solubility/water solubility, the administration route, the administration time, the release rate of the specific effective ingredient, the duration of the treatment, other drugs, compounds and/or substances used in combination therewith, age, sex, body weight, diseases, medical conditions, the patient's medical history, and other factors well-known in medicine. Usually, the dose of the composition for treatment of ALS for a patient is an amount including the effective ingredient at approximately 0.0001 to approximately 100 mg/kg of body weight per day. The composition for treatment of ALS may be administered once a day or separately approximately 2 to 4 times.

In particular, in a case where the therapeutic agent for ALS is the compound represented by Formula (2), for the dose of the composition for treatment of ALS, preferably, 2 mg of the active ingredient is orally administered once a day, the amount is increased every week, and the amount is to be orally administered within a range in which the effective ingredient does not exceed 16 mg per day.

Other Embodiments

In one embodiment, the present invention provides a method of treating ALS, including a step of administering an effective amount of a compound represented by Formula (1), a pharmaceutically acceptable salt thereof, or a solvate thereof to a patient in need of treatment. In the treatment method of the present embodiment, examples of the compound represented by Formula (1), the pharmaceutically acceptable salt thereof, or the solvate thereof are the same as those described above.

In one embodiment, the present invention provides the compound represented by Formula (1), a pharmaceutically acceptable salt thereof, or a solvate thereof, for the treatment of ALS. In the treatment method of the present embodiment, examples of the compound represented by Formula (1), a pharmaceutically acceptable salt thereof, or a solvate thereof are the same as described above.

In one embodiment, the present invention provides the use of a compound represented by Formula (1), a pharmaceutically acceptable salt thereof, or a solvate thereof, for producing a therapeutic agent for ALS. In the treatment method of the present embodiment, examples of the compound represented by Formula (1), the pharmaceutically acceptable salts thereof, or the solvates thereof are the same as described above.

EXAMPLES

Next, a more detailed description will be given of the present invention by showing Examples, but the present invention is not limited to the following Examples.

<I. Examination Using iPS Cells Derived from Familial ALS Patients>

Example I-1

(Differentiation into Motor Neurons)

It is known that familial ALS includes ALS caused by mutation of the FUS gene and ALS caused by mutation of the TDP-43 gene.

Therefore, iPS cells derived from healthy subjects, iPS cells derived from ALS patients having a mutation in FUS, and iPS cells derived from ALS patients having a mutation in TDP-43 were differentiated into motor neurons. The iPS cell lines used are as shown in Table 1 and were all derived from skin fibroblasts.

TABLE 1

| Derived From iPS Cells | Name of cell line |
|---|---|
| Healthy subject | 201B7 |
| | WD39 |
| | 409B2 |
| ALS patients having FUS mutation (H517D) | FALS-e46 |
| | FALS-e48 |
| | FALS-e54 |
| | FALS-2e2 |
| | FALS-2e3 |
| | FALS-2e23 |
| ALS patients having TDP-43 mutation (M337V) | A21412 |
| | A21428 |
| ALS patient having TDP-43 mutation (Q343R) | A3411 |
| | A3416 |

Specifically, each of the above cell lines was first cultured in a medium containing SB431542 (CAS number: 301836-41-9) at a final concentration of 3 μM, CHIR99021 (CAS number: 252917-06-9) at a final concentration of 3 μM, and Dorsomorphin (CAS No. 866405-64-3) at a final concentration of 3 μM for 5 days to induce differentiation-promoting pluripotent stem cells (DiSC). The medium was exchanged every day. Below, the time of starting the differentiation induction refers to the start of DiSC induction.

Subsequently, the obtained DiSC were dissociated into cells one by one and further cultured in a medium having the composition shown in Table 2 in a low-oxygen incubator for 7 days. The oxygen concentration was set at 5% (v/v). The medium was exchanged every 2 to 3 days.

TABLE 2

| |
|---|
| 1:1 mixture of DMEM medium and F-12 medium |
| 0.6% glucose |
| 2 mM glutamine |
| 3 mM sodium bicarbonate |
| 5 mM HEPES |
| 25 μg/mL insulin |
| 100 μg/mL transferrin |
| 20 nM progesterone |
| 30 nM selenium chloride |
| 60 μM putrescine |
| 2% B 27 supplement (Thermo Fisher Scientific) |
| 20 ng/mL bFGF |
| 10 μM Y-27632 (Wako Pure Chemical Industries) |
| 10 ng/mL hLIF |
| 3 μM CHIR99021 |
| 2 μM SB431542 |

Subsequently, the cells were further cultured in a medium having the composition shown in Table 3 in a low-oxygen incubator for 4 days. The oxygen concentration was set at 5% (v/v). The medium was exchanged every 2 to 3 days. DAPT (CAS number: 208255-80-5) was added to the medium on day 4 of culturing in the medium having the composition shown in Table 3 such that the final concentration was 5 μM.

TABLE 3

| |
|---|
| 1:1 mixture of DMEM medium and F-12 medium |
| 0.6% glucose |
| 2 mM glutamine |
| 3 mM sodium bicarbonate |
| 5 mM HEPES |
| 25 μg/mL insulin |
| 100 μg/mL transferrin |
| 20 nM progesterone |
| 30 nM selenium chloride |
| 60 μM putrescine |
| 2% B 27 supplement (Thermo Fisher Scientific) |
| 2 ng/mL bFGF |
| 10 μM Y-27632 (Wako Pure Chemical Industries) |
| 10 ng/mL hLIF |
| 2 μM SB431542 |
| 2 μM retinoic acid |
| 1 μM palmorphamine (CAS number: 483367-10-8) |

On day 14 of culturing with the medium having the composition shown in Table 3, the cells were again dissociated one by one, and further cultured for 5 to 40 days in a neuron differentiation induction medium having the composition shown in Table 4. This induced differentiation into motor neurons.

TABLE 4

| |
|---|
| 1:1 mixture of DMEM medium and F-12 medium |
| 0.6% glucose |
| 2 mM glutamine |
| 3 mM sodium bicarbonate |
| 5 mM HEPES |
| 25 μg/mL insulin |
| 100 μg/mL transferrin |
| 20 nM progesterone |
| 30 nM selenium chloride |
| 60 pM putrescine |
| 2% B 27 supplement (Thermo Fisher Scientific) |
| 10 ng/mL Brain-derived neurotrophic factor (BDNF, R & D Systems) |
| 10 ng/mL Glial cell-derived neurotrophic factor (GDNF, R & D Systems) |
| 1 μM retinoic acid |
| 2 μM DAPT (CAS number: 208255-80-5) |
| 200 ng/mL ascorbic acid |

Using the differentiation-induced motor neurons, the expression levels of each gene were examined for Neurogenic differentiation 1 (NeuroD1), SRY-Box 1 (SOX 1), Oligodendrocyte Lineage Transcription Factor 2 (OLIG 2), LIM Homeobox 3 (LHX 3), ISLET 1, HB9, and Choline acetyltransferase (ChAT). Spinal cord tissue was used as a positive control. As a result, it was confirmed that the obtained motor neurons exhibited gene expression patterns similar to the spinal cord. From these results, it was confirmed that it was possible to induce iPS cells to differentiate into motor neurons.

In addition, differentiation-induced motor neurons were immunostained and the expression of Glial Fibrillary Acidic Protein (GFAP), βII-tubulin, HB9, and ChAT was examined. As a result, it was confirmed from the result of immunostaining that it was possible to induce the iPS cells to differentiate into motor neurons.

Example I-2

(Analysis of Neurite Length)

For each differentiation-induced motor neuron in Example I-1, the changes over time in the neurite length were measured. A Bio station CT (Nikon Corp.) was used to measure the neurite length over time. FIG. 1 is a graph showing measurement results of changes over time in the neurite length. The vertical axis represents neurite length (relative value), and the horizontal axis represents the number of days of culturing from the start of differentiation induction. As a result, it was revealed that, in the motor neurons induced to differentiate from iPS cells derived from healthy subjects, the neurite length was continuously increased, while in the motor neurons induced to differentiate from iPS cells derived from the ALS patients, the neurite length was shortened with approximately 40 days after the start of induction of differentiation as the peak. This result indicates that the differentiation-induced motor neurons mirror the ALS disease.

Example I-3

(Analysis of Cleaved Type Caspase 3-Positive Ratio)

On day 40 from the start of induction of differentiation, each differentiation-induced motor neuron in Example I-1 was immunostained using antibodies with respect to cleaved type (Cleaved, CV) caspase 3 (may be referred to as "CV caspase 3"), and the ratio of cleaved type (Cleaved, CV) caspase 3 (may be referred to as "CV caspase 3")-positive neurons was measured. CV caspase 3-positive neurons are neurons for which apoptosis was induced.

Figure 2:
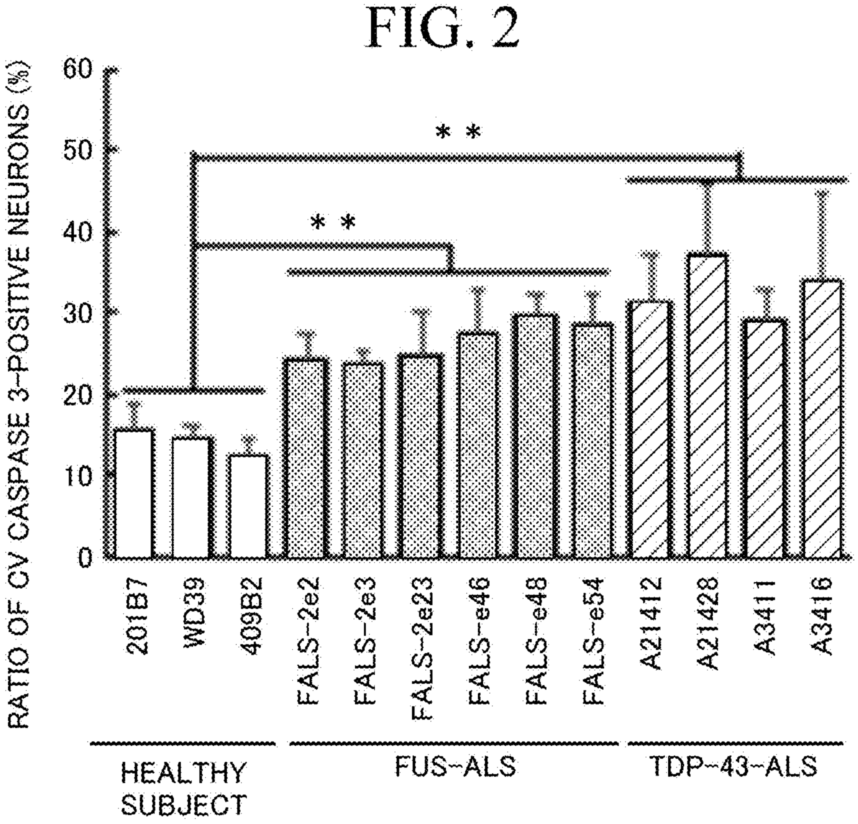
FIG. 2 is a graph showing a ratio of CV caspase 3-positive neurons in each motor neuron measured in Example I-3.

FIG. 2 is a graph showing the ratio of CV caspase 3-positive neurons in each motor neuron. In the diagram, "**" indicates that there is a significant difference when the risk is less than 1%. As a result, it was revealed that, in comparison with motor neurons induced to differentiate from iPS cells derived from healthy subjects, the ratio of CV caspase 3-positive neurons was significantly higher in motor neurons induced to differentiate from iPS cells derived from ALS patients. This result further supports the differentiation-induced motor neurons mirroring the ALS disease.

Example I-4

(Analysis of LDH Leakage Ratio)

On day 40 from the start of differentiation induction, the leakage of lactate dehydrogenase (LDH) from the cells was measured using each differentiation-induced motor neuron in Example I-1. The leakage amount of LDH into the medium is an indicator of cytotoxicity. For measurement of the LDH leakage ratio, a commercially available kit (model "LDH Cytotoxicity Detection Kit", Takara Bio Inc.) was used.

Figure 3:
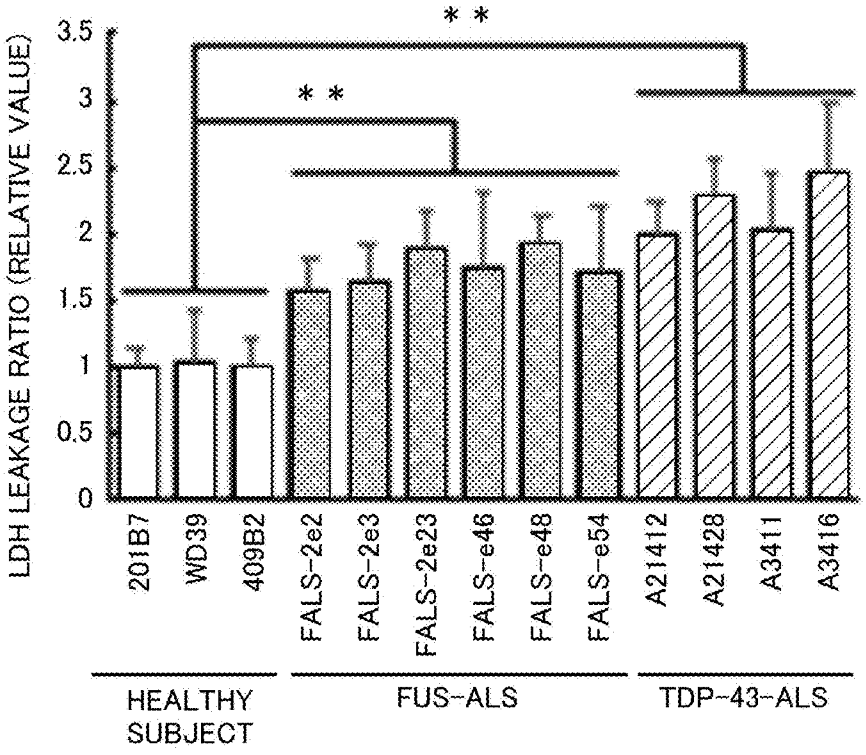
FIG. 3 is a graph showing a LDH leakage ratio in each motor neuron measured in Example I-4.

FIG. 3 is a graph showing the measurement results (relative value) of the LDH leakage ratio in each motor neuron. In the diagram, "**" indicates that there is a significant difference when the risk is less than 1%. As a result, it was revealed that, in comparison with motor neurons induced to differentiate from iPS cells derived from healthy subjects, the LDH leakage ratio was significantly higher in motor neurons induced to differentiate from iPS cells derived from ALS patients. This result further supports the differentiation-induced motor neurons mirroring the ALS disease.

Example I-5

(Analysis of Localization of FUS Protein)

The FUS protein is an RNA binding protein localized in the nucleus. In contrast, it is known that ectopic localization of the FUS protein in the cytoplasm is observed in ALS patients having a mutation in FUS.

Therefore, on day 40 from the start of differentiation induction, each differentiation-induced motor neuron in Example I-1 was immunostained and the localization of FUS protein in the cytoplasm was examined.

Figure 4:
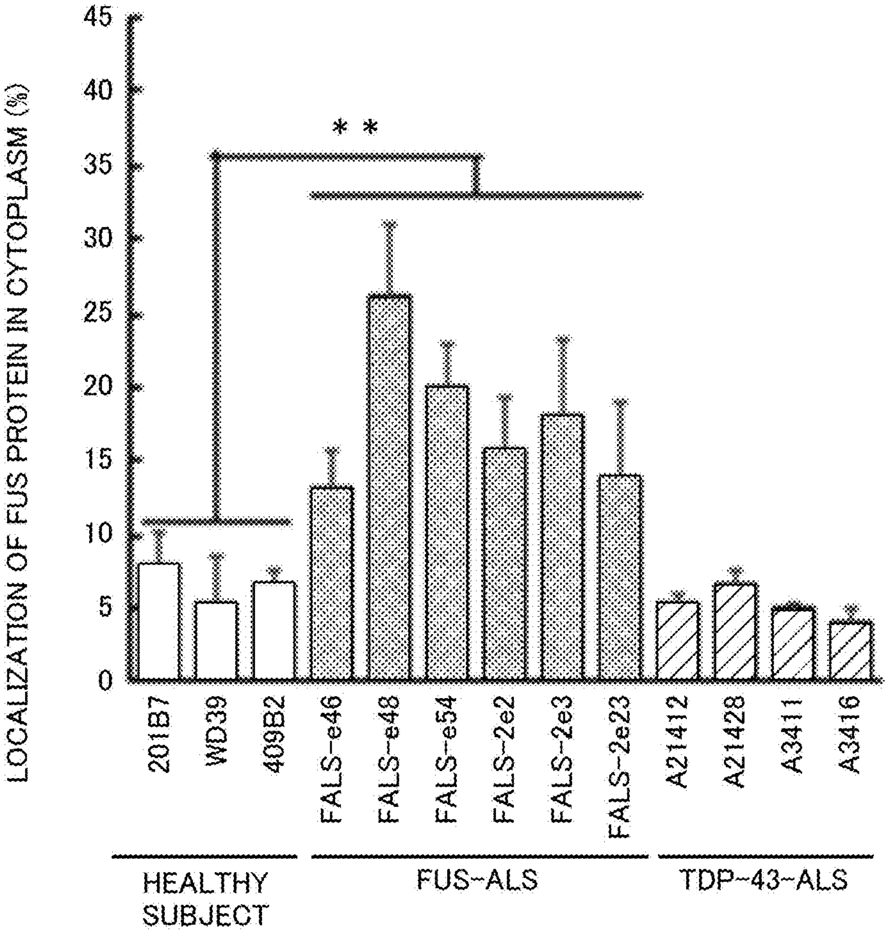
FIG. 4 is a graph showing the results of measuring the ratio of motor neurons in which localization of FUS protein in the cytoplasm was observed in Example I-5.

FIG. 4 is a graph showing the results of measurement of the ratio of neurons in which localization of FUS protein in the cytoplasm was observed in each motor neuron. In the diagram, "**" indicates that there is a significant difference when the risk is less than 1%.

As a result, it was revealed that, in comparison with motor neurons induced to differentiate from iPS cells derived from healthy subjects, the ratio of neurons in which localization of the FUS protein in the cytoplasm was observed was significantly higher in motor neurons induced to differentiate from iPS cells derived from ALS patients (FUS-ALS) having a mutation in FUS.

On the other hand, in motor neurons induced to differentiate from iPS cells derived from ALS patients (TDP-43-ALS) having a mutation in TDP-43, no significant increase in the localization of the FUS protein in the cytoplasm was observed.

This result further supports differentiation-induced motor neurons mirroring the ALS disease with mutations in FUS.

Example I-6

(Formation of Inclusions of Phosphorylated TDP-43 Protein)

The TDP-43 protein is an RNA binding protein localized in the nucleus. In ALS patients having a mutation in TDP-43, it is known that inclusions of abnormally phosphorylated TDP-43 protein are visible.

Therefore, on day 40 from the start of differentiation induction, each differentiation-induced motor neuron in Example I-1 was immunostained and the formation of phosphorylated TDP-43 protein inclusions was examined.

Figure 5:
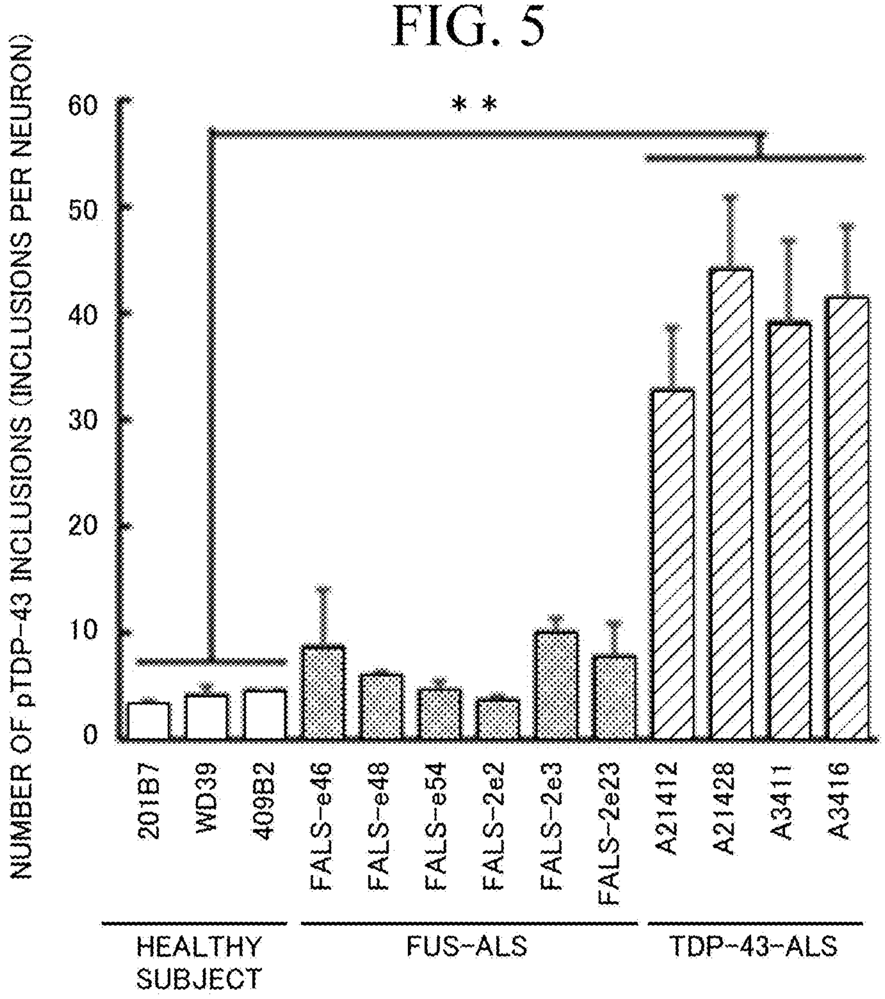
FIG. 5 is a graph showing the results of measuring the number of inclusions of phosphorylated TDP-43 protein per motor neuron in Example I-6.

FIG. 5 is a graph showing the results of measuring the number of inclusions of phosphorylated TDP-43 protein (pTDP-43) per neuron in each motor neuron. In the diagram, "**" indicates that there is a significant difference when the risk is less than 1%.

As a result, it was revealed that, in comparison with motor neurons induced to differentiate from iPS cells derived from healthy subjects, in motor neurons induced to differentiate from iPS cells derived from ALS patients (TDP-43-ALS) having a mutation in TDP-43, the number of inclusions of the phosphorylated TDP-43 protein per neuron was significantly increased.

On the other hand, in motor neurons induced to differentiate from iPS cells derived from ALS patients (FUS-ALS) having a mutation in FUS, no significant increase in the number of inclusions of phosphorylated TDP-43 protein was observed.

This result further supports differentiation-induced motor neurons mirroring the ALS disease with mutations in TDP-43.

Example I-7

(Analysis of Stress Granules)

On day 40 from the start of differentiation induction, the formation of stress granules was examined using each differentiation-induced motor neuron in Example I-1. The detection of stress granules was performed by immunostaining with G3BP, which is a marker of stress granules.

Figure 6:
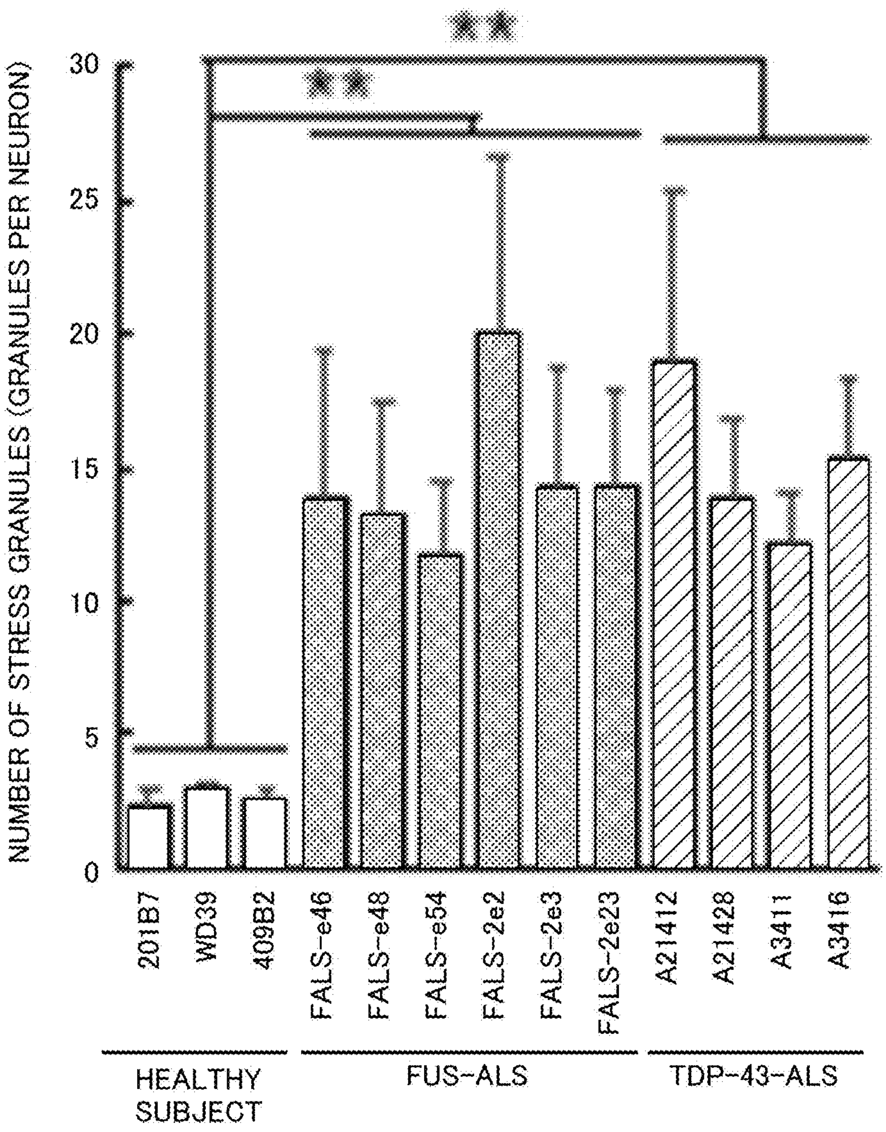
FIG. 6 is a graph showing the number of stress granules per motor neuron measured in Example I-7.

FIG. 6 is a graph showing the measurement results of the number of stress granules per neuron in each motor neuron. In the diagram, "**" indicates that there is a significant difference when the risk is less than 1%. As a result, it was revealed that, in comparison with motor neurons induced to differentiate from iPS cells derived from healthy subjects, the number of stress granules per neuron was significantly increased in motor neurons induced to differentiate from iPS cells derived from ALS patients. This result further supports the differentiation-induced motor neurons mirroring the ALS disease.

Example I-8

(Screening of Therapeutic Agent for ALS)

Using the differentiation-induced motor neurons in Example I-1, drugs which cause the ALS phenotype to be restored were screened from existing drug libraries with the neurite length, ectopic localization of FUS protein, stress granule formation, LDH leakage ratio, CV-caspase 3-positive ratio, phosphorylated TDP-43 protein inclusion formation, and the like as indices.

As a result of the screening, ropinirole was found as a promising therapeutic agent for ALS. Tables 5 and 6 show the improvement ratio (%) in the ALS phenotype due to adding ropinirole to the medium. Here, ropinirole was added to the medium on days 35 to 40 from the start of the differentiation induction of each iPS cell. Here, it is assumed that days 35 to 40 from the start of differentiation induction correspond to the early stage of the ALS disease.

The improvement ratio (%) of the ALS phenotype was calculated by Equation (1).

$$\text{Improvement ratio } (\%) = (A - B)/(A - C) \times 100 \quad (1)$$

[In Equation (1), A represents a measurement value of motor neurons induced to differentiate from iPS cells derived from ALS patients in the absence of ropinirole, and B represents a measurement value of motor neurons induced to differentiate from iPS cells derived from ALS patients in the presence of ropinirole, and C represents a measurement value of motor neurons induced to differentiate from iPS cells derived from healthy subjects in the absence of ropinirole.]

Table 5 shows the results of adding ropinirole at final concentrations of 0.1, 1, and 10 μM to a medium of motor neurons induced and differentiated from iPS cells derived from ALS patients (FUS-ALS) having a mutation in FUS, and Table 6 shows the results of adding ropinirole at final concentrations of 0.1, 1, and 10 μM to a medium of motor neurons induced to differentiate from iPS cells derived from ALS patients (TDP-43-ALS) having a mutation in TDP-43.

TABLE 5

| Derived from FUS-ALS | | | | |
|---|---|---|---|---|
| Final concentration of Ropinirole (μM) | Neurite length improvement ratio (%) | Ectopic localization of FUS protein improvement ratio (%) | Stress granule formation improvement ratio (%) | LDH leakage ratio improvement ratio (%) |
| 0.1 | 43.3 | 55.8 | 36.6 | 33.5 |
| 1 | 58.3 | 54.3 | 34.4 | 48.0 |
| 10 | 61.3 | 74.4 | 66.1 | 47.6 |

TABLE 6

| Derived from TDP-43-ALS | | | | |
|---|---|---|---|---|
| Final concentration of Ropinirole (μM) | Neurite length improvement ratio (%) | CV Caspase 3-positive ratio improvement ratio (%) | TDP-43 inclusion formation improvement ratio (%) | LDH leakage ratio improvement ratio (%) |
| 0.1 | 50.4 | 74.3 | 56.2 | 58.3 |
| 1 | 75.3 | 70.3 | 69.2 | 78.1 |
| 10 | 77.2 | 87.9 | 74.2 | 82.4 |

As shown in Tables 5 and 6, it was revealed that ropinirole exhibits a remarkable improvement effect on both ALS having a mutation in FUS and ALS having a mutation in TDP-43.

Subsequently, in the same manner as above, the efficacy in cases of administering lower concentrations of ropinirole was evaluated. Table 7 shows the results of adding ropinirole at final concentrations of 0.1, 1, 10 nM to a medium of motor neurons induced to differentiate from iPS cells derived from ALS patient (FUS-ALS) having a mutation in FUS, and Table 8 shows the results of adding ropinirole at final concentrations of 0.1, 1, and 10 nM to a medium of motor neurons induced to differentiate from iPS cells derived from ALS patient (TDP-43-ALS) having a mutation in TDP-43.

TABLE 7

| Derived from FUS-ALS | | | | |
|---|---|---|---|---|
| Final concentration of Ropinirole (nM) | Neurite length improvement ratio (%) | Ectopic localization of FUS protein improvement ratio (%) | Stress granule formation improvement ratio (%) | LDH leakage ratio improvement ratio (%) |
| 0.1 | 3.22 | 20.2 | 8.2 | 10.1 |
| 1 | 32.3 | 45.8 | 23.2 | 31.1 |
| 10 | 45.8 | 51.2 | 39.3 | 39.4 |

TABLE 8

| Derived from TDP-43-ALS | | | | |
|---|---|---|---|---|
| Final concentration of Ropinirole (nM) | Neurite length improvement ratio (%) | CV Caspase 3-positive ratio improvement ratio (%) | TDP-43 inclusion formation improvement ratio (%) | LDH leakage ratio improvement ratio (%) |
| 0.1 | 12.1 | 21.9 | 15.3 | 10.2 |
| 1 | 49.4 | 59.8 | 55.3 | 55.2 |
| 10 | 52.3 | 69.2 | 60.3 | 56.6 |

As shown in Tables 7 and 8, it was revealed that ropinirole exhibits improvement effects on both ALS having a mutation in FUS and ALS having a mutation in TDP-43 even at the final concentrations of 0.1 to 10 nM, in particular, exhibiting remarkable improvement effects for all items at 1 to 10 nM.

In addition, Tables 9 and 10 below show the results of performing the same examination as above except that, instead of ropinirole, riluzole and edaravone, which are existing ALS drugs, and ceftriaxone, a drug previously used for clinical studies of ALS were added. Each drug was added to the medium at a final concentration of 10 μM.

Table 9 shows the results of adding each drug to the medium of motor neurons induced to differentiate from iPS cells derived from ALS patients (FUS-ALS) having a mutation in FUS. In addition, Table 10 shows the results of adding each drug to a medium of motor neurons induced to differentiate from iPS cells derived from ALS patients (TDP-43-ALS) having a mutation in TDP-43.

TABLE 9

| Derived from FUS-ALS | | | | |
|---|---|---|---|---|
| Drug | Neurite length improvement ratio (%) | Ectopic localization of FUS protein improvement ratio (%) | Stress granule formation improvement ratio (%) | LDH leakage ratio improvement ratio (%) |
| Riluzole | 8.89 | 6.83 | 9.38 | 5.83 |
| Edaravone | 15.9 | 20.4 | 19.8 | 12.4 |
| Ceftriaxone | 36.3 | 22.6 | 11.0 | 21.2 |

TABLE 10

| Derived from TDP-43-ALS | | | | |
|---|---|---|---|---|
| Drug | Neurite length improvement ratio (%) | CV Caspase 3-positive ratio improvement ratio (%) | TDP-43 inclusion formation improvement ratio (%) | LDH leakage ratio improvement ratio (%) |
| Riluzole | 0.277 | 0.113 | 10.3 | −11.7 |
| Edaravone | 14.2 | 11.2 | 11.6 | 23.2 |
| Ceftriaxone | 20.4 | 18.1 | 35.4 | 15.1 |

As a result, it was revealed that ropinirole exhibits more remarkable improvement effects on both ALS having a mutation in FUS and ALS having a mutation in TDP-43 in comparison with riluzole, edaravone, and ceftriaxone.

Example I-9

(Evaluation of Efficacy of Ropinirole in Late Stage ALS Disease)

The efficacy of ropinirole was evaluated in the same manner as in Example I-8, except that the timing of adding ropinirole was changed to days 50 to 62 from the start of the differentiation induction of each iPS cell. It is assumed that days 50 to 62 after the start of induction of differentiation correspond to the late stage of the ALS disease.

Specifically, ropinirole was added to a medium of motor neurons induced to differentiate from iPS cells derived from ALS patients (FUS-ALS) having a mutation in FUS and motor neurons induced to differentiate from iPS cells derived from ALS patients (TDP-43-ALS) having a mutation in TDP-43 and the changes over time in the neurite length were measured. The measurement of neurite length was carried out in the same manner as in Example I-2. Ropinirole was added to the medium at a final concentration of 1 μM.

Figure 14:
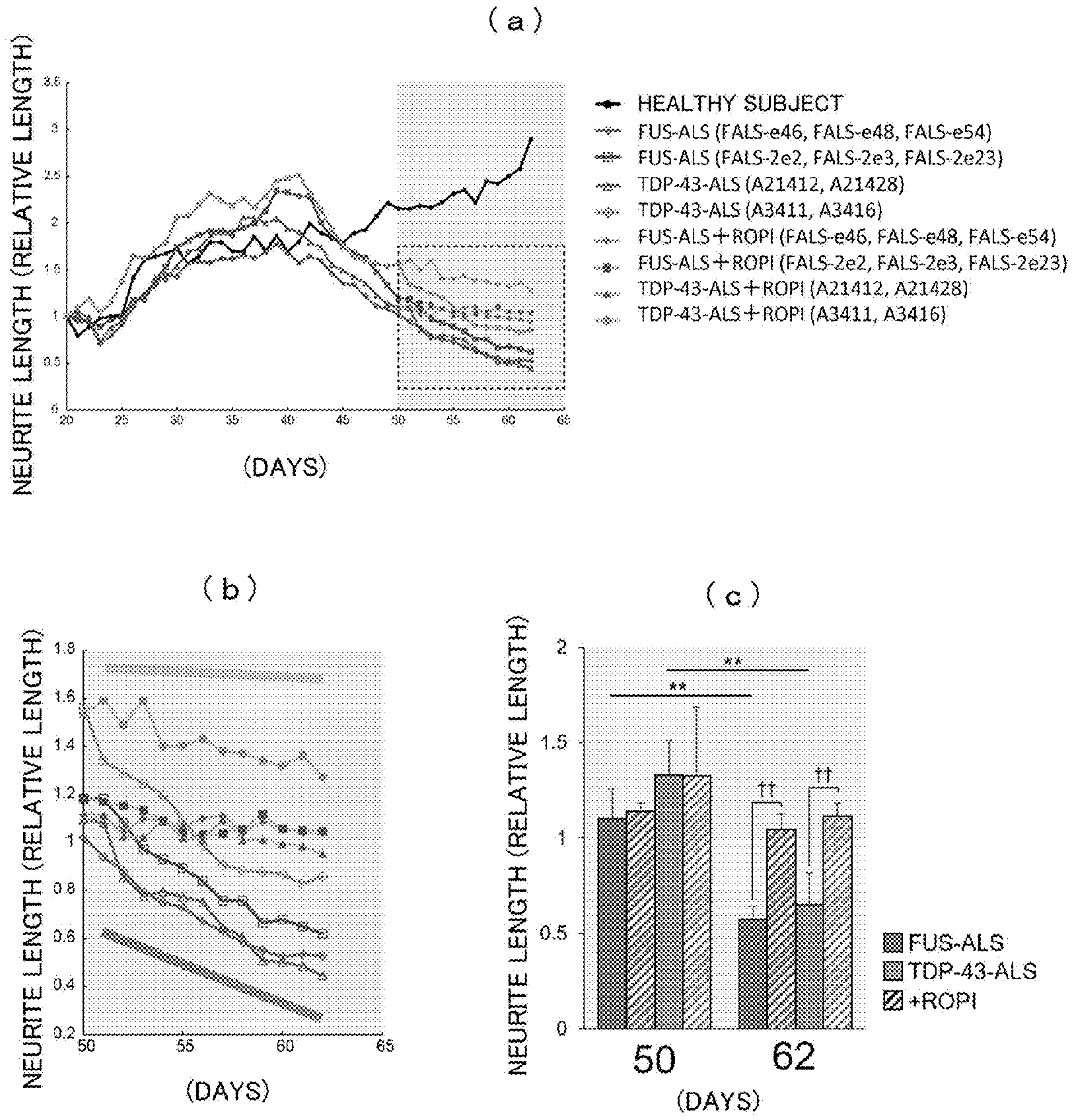
FIG. 14(*a*) is a graph showing changes over time in the neurite length of each motor neuron measured in Example I-9.

FIG. 14(*a*) is a graph showing the results of measurement of the changes over time in the neurite length of each motor neuron. In FIG. 14(*a*), the vertical axis represents the neurite length (relative value), the horizontal axis represents the number of days of culturing from the start of differentiation induction, and "+ROPI" represents the result of adding ropinirole to the medium. In addition, FIG. 14(*b*) is a graph enlarging the boxed portion of the graph of FIG. 14(*a*). In addition, FIG. 14(*c*) is a graph showing the neurite length of each motor neuron on day 50 and day 62 from the start of differentiation induction. In FIG. 14(*c*), "**" and "++" indicate that there is a significant difference when the risk is less than 1%, and "+ROPI" represents the result of adding ropinirole to the medium.

As a result, even on days 50 to 62 from the start of differentiation induction, a neuroprotective action (maintenance of neurite length) due to the addition of ropinirole was observed. This result indicates that ropinirole has an effect of improving the ALS disease even in the late stage of the ALS disease.

<II. Examination Using iPS Cells Derived from Sporadic ALS Patients>

Example II-1

(Differentiation into Motor Neurons)

In the same manner as in Example I-1, iPS cells derived from sporadic ALS (may be referred to below as "SALS") patients were differentiated into motor neurons. All the iPS cells used were derived from dermal fibroblasts. Clinical information on the patients from whom the used iPS cells were derived is shown in Table 11. Below, each differentiated motor neuron is identified by the patient number from whom the neuron was derived.

TABLE 11

| Patient number | Onset age | Gender | Family history | Clinical type |
|---|---|---|---|---|
| 001-0218 | 54.9 | Male | None | UMN |
| 001-0324 | 40.2 | Male | None | UMN |
| 001-0431 | 59.6 | Female | None | UMN |

Example II-2

(Analysis of Neurite Length)

With respect to each of the differentiation-induced motor neurons in Example II-1, the changes over time in the neurite length were analyzed in the same manner as in Example I-2. As a result, it was revealed that, on days 40 to 45 from the start of differentiation induction, the neurite length, which had until then continued to elongate, was shortened. This result shows that the differentiation-induced motor neurons mirror the ALS disease.

Example II-3

(Analysis of LDH Leakage Ratio)

The leakage ratio of LDH from cells was measured over time using each differentiation-induced motor neuron in Example II-1. The LDH leakage ratio was measured in the same manner as in Example I-4.

Figure 7:
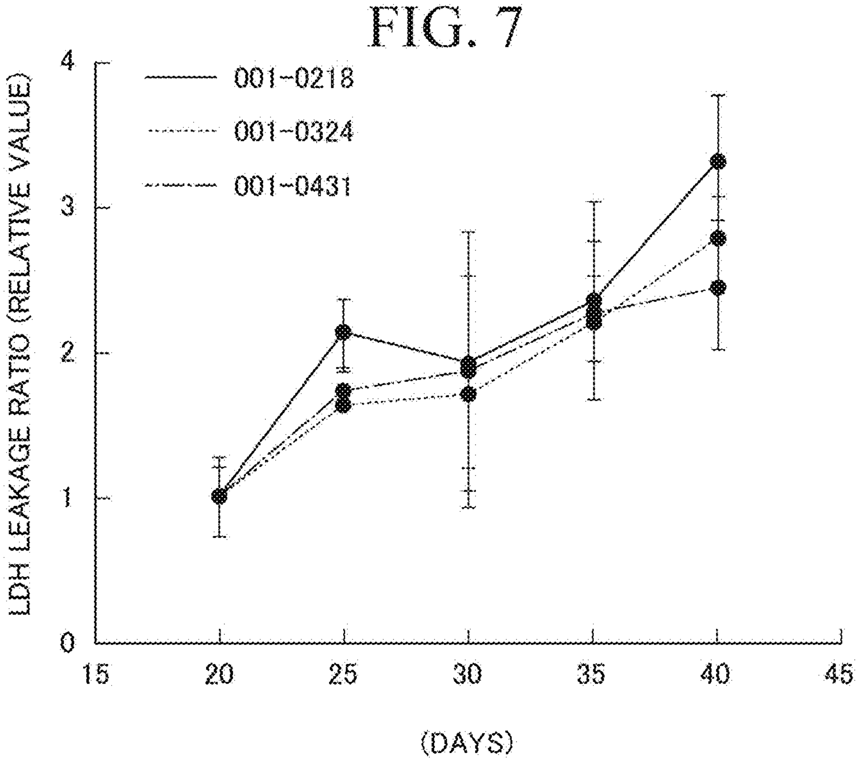
FIG. 7 is a graph showing changes over time in the LDH leakage ratio in each motor neuron measured in Example II-3.

FIG. 7 is a graph showing changes over time in the LDH leakage ratio (relative value) in each motor neuron. The horizontal axis shows the number of days since the start of differentiation induction. As a result, it was revealed that the LDH leakage ratio increases over time in motor neurons induced to differentiate from iPS cells derived from sporadic ALS patients. This result further supports the differentiation-induced motor neurons mirroring the ALS disease.

Example II-4

(Analysis of CV Caspase 3-Positive Ratio)

Using each differentiation-induced motor neuron in Example II-1, the ratio of CV caspase 3-positive neurons was measured over time in the same manner as in Example I-3.

Figure 8:
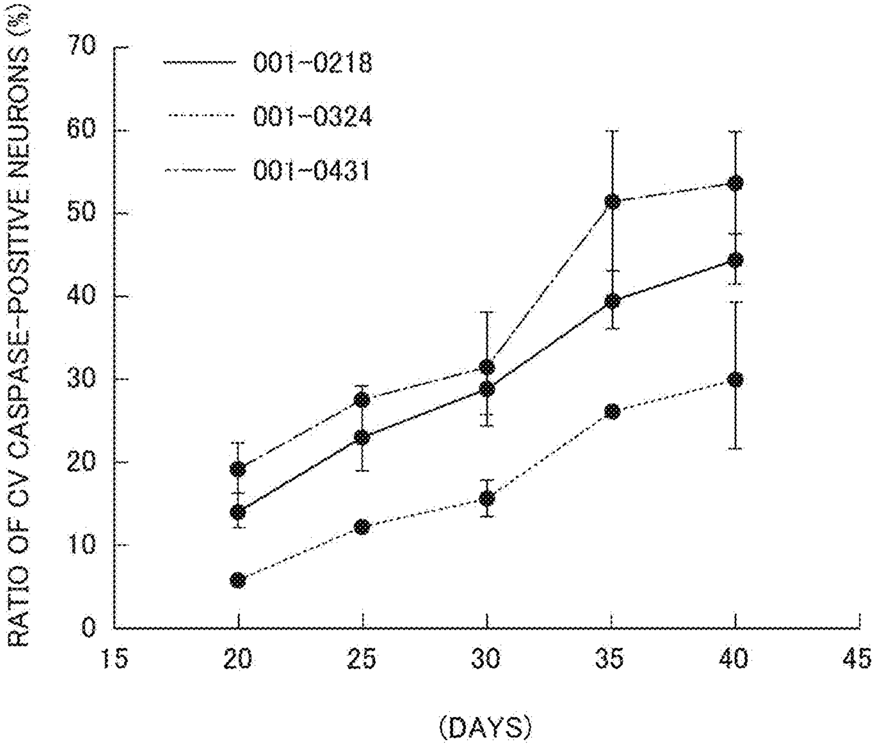
FIG. 8 is a graph showing changes over time in the ratio of CV caspase 3-positive neurons in each motor neuron measured in Example II-4.

FIG. 8 is a graph showing the changes over time in the ratio of CV caspase 3-positive neurons in each motor neuron. The horizontal axis shows the number of days since the start of differentiation induction. As a result, it was revealed that, in motor neurons induced to differentiate from iPS cells derived from sporadic ALS patients, the ratio of CV caspase 3-positive neurons increases over time. This result further supports the differentiation-induced motor neurons mirroring the ALS disease.

Example II-5

(Analysis of Stress Granules)

Using each differentiation-induced motor neuron in Example II-1, the formation of stress granules was measured over time in the same manner as in Example I-7.

Figure 9:
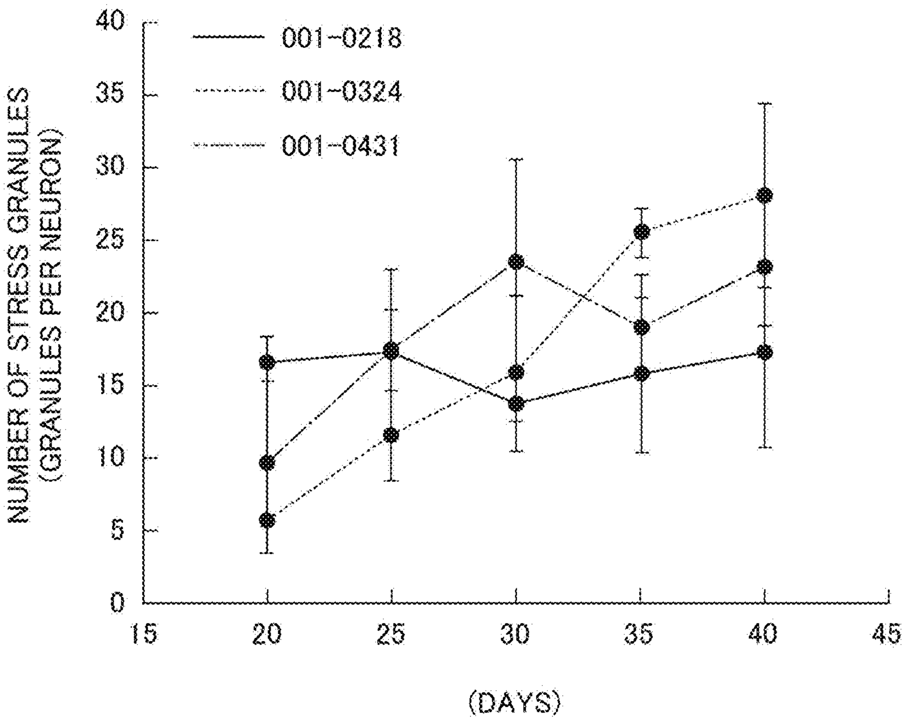
FIG. 9 is a graph showing changes over time in the number of stress granules per motor neuron measured in Example II-5.

FIG. 9 is a graph showing the changes over time in the number of stress granules per neuron in each motor neuron. The horizontal axis shows the number of days since the start of differentiation induction. As a result, it was revealed that, in motor neurons induced to differentiate from iPS cells derived from sporadic ALS patients, the number of stress granules increases over time. This result further supports the differentiation-induced motor neurons mirroring the ALS disease.

<III. Evaluation of Efficacy of Ropinirole Using Sporadic ALS Model>

Example III-1

(Analysis of Neurite Length)

In the same manner as in Example II-1, iPS cells derived from sporadic ALS (SALS) patients were induced to differentiate into motor neurons, and then ropinirole with a final concentration of 1 μM was added to the medium. More specifically, for the period of days 35 to 40 from the start of differentiation induction, ropinirole having a final concentration of 1 μM was added to the medium. In addition, a group for which ropinirole was not added to the medium was prepared as a control. In addition, for comparison, iPS cells derived from healthy subjects were differentiated into motor neurons in the same manner as in Example I-1. No ropinirole was added to the medium of these motor neurons. As the iPS cells derived from a healthy subject, the same cells as used in Example I-1 were used.

Subsequently, on day 40 from the start of differentiation induction, the neurite length was measured for each motor neuron in the same manner as in Example I-2.

Figure 10:
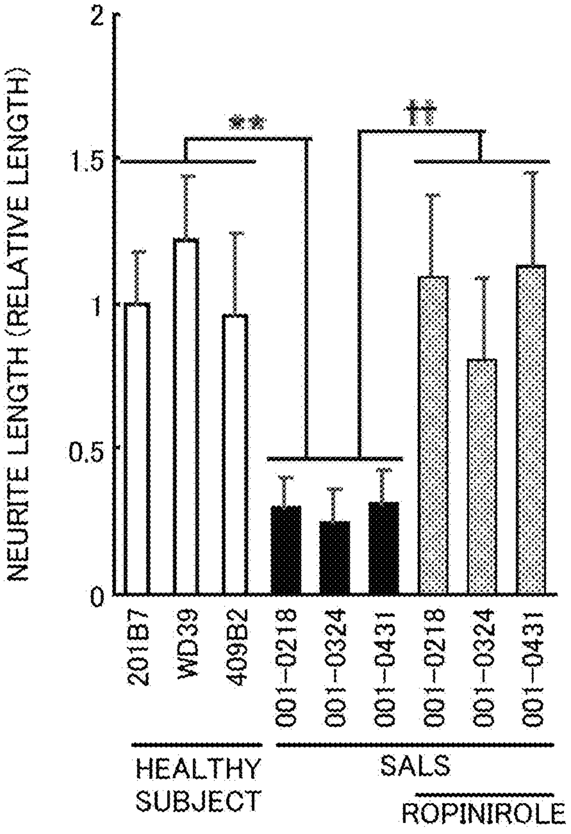
FIG. 10 is a graph showing the neurite length of each motor neuron measured in Example III-1.

FIG. 10 is a graph showing measurement results of the neurite length of each motor neuron. In the diagram, "**" and "++" indicate that there is a significant difference when the risk is less than 1%. As a result, it was revealed that, in the presence of ropinirole, neurite length reduction in motor neurons induced to differentiate from iPS cells derived from SALS patients was significantly suppressed.

This result shows that ropinirole is effective not only for familial ALS but also for sporadic ALS treatment.

Example III-2

(Analysis of CV caspase 3-Positive Ratio)

In the same manner as in Example II-1, iPS cells derived from sporadic ALS (SALS) patients were induced to differentiate into motor neurons, and then ropinirole with a final concentration of 1 μM was added to the medium. More specifically, for the period of days 35 to 40 from the start of differentiation induction, ropinirole having a final concentration of 1 μM was added to the medium. In addition, a group for which ropinirole was not added to the medium was prepared as a control. In addition, for comparison, iPS cells derived from healthy subjects were differentiated into motor neurons in the same manner as in Example I-1. No ropinirole was added to the medium of these motor neurons. As the iPS cells derived from a healthy subject, the same cells as used in Example I-1 were used.

Subsequently, on day 40 from the start of differentiation induction, the ratio of CV caspase 3-positive neurons was measured for each motor neuron in the same manner as in Example I-3.

Figure 11:
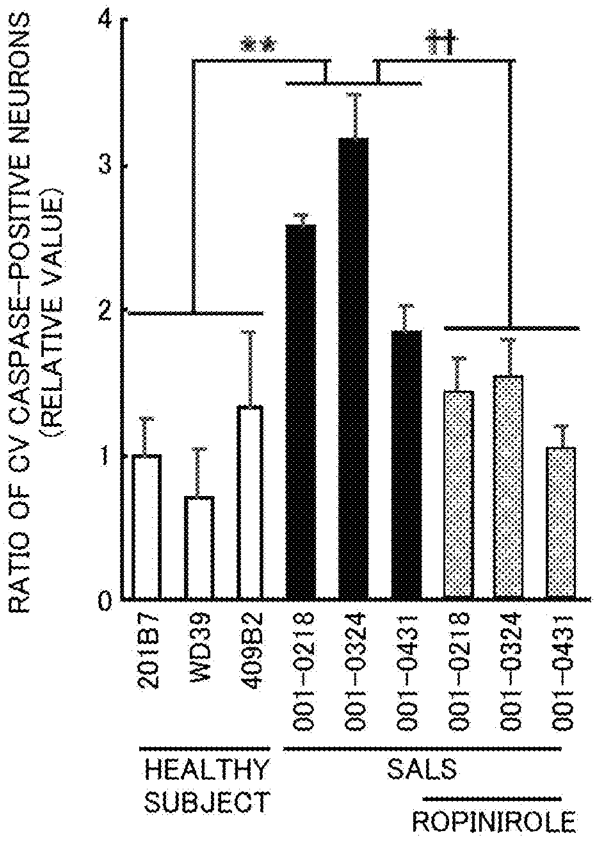
FIG. 11 is a graph showing the ratio of CV caspase 3-positive neurons measured in Example III-2.

FIG. 11 is a graph showing the measurement results of the ratio of CV caspase 3-positive neurons. In the diagram, "**" and "++" indicate that there is a significant difference when the risk is less than 1%. As a result, it was revealed that, in the presence of ropinirole, the ratio of CV caspase 3-positive neurons in motor neurons induced to differentiate from iPS cells derived from SALS patients was significantly reduced.

This result further supports ropinirole being effective not only for familial ALS but also for sporadic ALS treatment.

Example III-3

(Analysis of LDH Leakage Ratio)

In the same manner as in Example II-1, iPS cells derived from sporadic ALS (SALS) patients were induced to differentiate into motor neurons, and then ropinirole with a final concentration of 1 μM was added to the medium. More specifically, for the period of days 35 to 40 from the start of differentiation induction, ropinirole having a final concentration of 1 μM was added to the medium. In addition, a group for which ropinirole was not added to the medium was prepared as a control. In addition, for comparison, iPS cells derived from healthy subjects were differentiated into motor neurons in the same manner as in Example I-1. No ropinirole was added to the medium of these motor neurons. As the iPS cells derived from a healthy subject, the same cells as used in Example I-1 were used.

Subsequently, on day 40 from the start of differentiation induction, the LDH leakage ratio was measured for each motor neuron in the same manner as in Example I-4.

Figure 12:
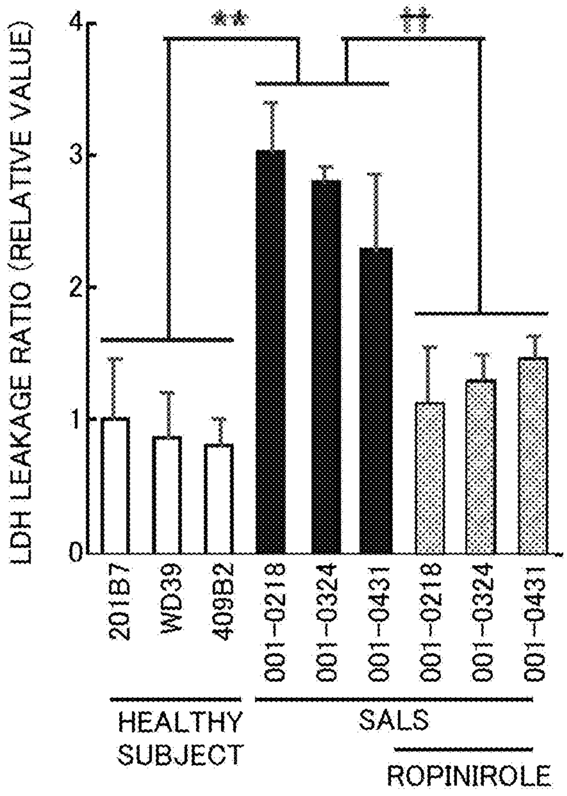
FIG. 12 is a graph showing the LDH leakage ratio of each motor neuron measured in Example III-3.

FIG. 12 is a graph showing the measurement result of the LDH leakage ratio. In the diagram, "**" and "++" indicate that there is a significant difference when the risk is less than 1%. As a result, it was revealed that, in the presence of ropinirole, the LDH leakage ratio in motor neurons induced to differentiate from iPS cells derived from SALS patients was significantly decreased.

This result further supports ropinirole being effective not only for familial ALS but also for sporadic ALS treatment.

Example III-4

(Analysis of Stress Granules)

In the same manner as in Example II-1, iPS cells derived from sporadic ALS (SALS) patients were induced to differentiate into motor neurons, and ropinirole with a final concentration of 1 μM was added to the medium. More specifically, for the period of days 35 to 40 from the start of differentiation induction, ropinirole having a final concentration of 1 μM was added to the medium. In addition, a group for which ropinirole was not added to the medium was prepared as a control. In addition, for comparison, iPS cells derived from healthy subjects were differentiated into motor neurons in the same manner as in Example I-1. No ropinirole was added to the medium of these motor neurons. As the iPS cells derived from a healthy subject, the same cells as used in Example I-1 were used.

Subsequently, on day 40 from the start of differentiation induction, the number of stress granules was measured for each motor neuron in the same manner as in Example I-7.

Figure 13:
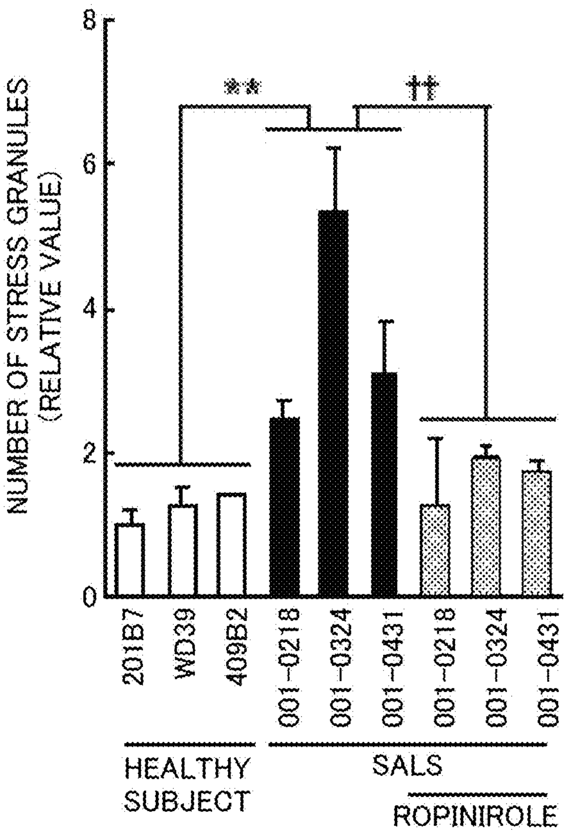
FIG. 13 is a graph showing the number of stress granules of each motor neuron measured in Example III-4.

FIG. 13 is a graph showing the measurement result of the number of stress granules. In the diagram, "**" and "++" indicate that there is a significant difference when the risk is less than 1%. As a result, it was revealed that, the number of stress granules in motor neurons induced to differentiate from iPS cells derived from SALS patients significantly decreased in the presence of ropinirole.

This result further supports ropinirole being effective not only for familial ALS but also for sporadic ALS treatment.

Example III-5

(Evaluation of Efficacy of Ropinirole Using Sporadic ALS Model)

In the same manner as in Example II-1, iPS cells derived from 24 patients having sporadic ALS (SALS) were differentiated into motor neurons and then ropinirole with a final concentration of 1 μM was added to the medium. In addition, for comparison, a group for which ropinirole was not added to the medium was prepared. In addition, as a control, a group for which iPS cells derived from healthy subjects were differentiated into motor neurons in the same manner as in Example I-1 was used. No ropinirole was added to the medium of these motor neurons. As the iPS cells derived from a healthy subject, the same cells as used in Example I-1 were used.

The following Table 12 shows the clinical information of patients from which the iPS cells used were derived. Below, each differentiated motor neuron is identified by the patient number from whom the neuron was derived.

TABLE 12

| Patient number | Onset age | Gender | Family history | Clinical type |
|---|---|---|---|---|
| SALS-2 | 78.3 | Male | None | Bulbar |
| SALS-4 | 50.1 | Male | None | UMN |
| SALS-5 | 39.1 | Male | None | Bulbar |
| SALS-6 | 62.3 | Male | None | Bulbar |
| SALS-7 | 59.3 | Male | None | Bulbar |
| SALS-9 | 40.3 | Male | None | Bulbar |
| SALS-10 | 65.8 | Female | None | UMN |
| SALS-12 | 48.7 | Male | None | LMN |
| SALS-14 | 57.7 | Female | None | LMN |
| SALS-15 | 55.1 | Female | None | LMN |

TABLE 12-continued

| Patient number | Onset age | Gender | Family history | Clinical type |
|---|---|---|---|---|
| SALS-16 | 67.2 | Male | None | Dropped head |
| SALS-17 | 60.3 | Male | None | LMN |
| SALS-19 | 59.6 | Female | None | UMN |
| SALS-20 | 46.5 | Male | None | UMN |
| SALS-21 | 38.6 | Female | None | Bulbar |
| SALS-22 | 64.8 | Female | None | Bulbar |
| SALS-23 | 60.9 | Male | None | Bulbar |
| SALS-26 | 55.6 | Female | None | UMN |
| SALS-27 | 36.7 | Male | None | UMN |
| SALS-28 | 47.7 | Female | None | LMN |
| SALS-29 | 47.9 | Male | None | UMN |
| SALS-30 | 65.8 | Female | None | LMN |
| SALS-31 | 46.7 | Male | None | UMN |
| SALS-32 | 60.8 | Male | None | UMN |

In all of the motor neurons, the addition period of ropinirole was 5 days. The time to start the addition of ropinirole varied depending on the case and was from day 30 to day 70 from the start of the differentiation induction of each of the iPS cells.

Subsequently, for each motor neuron on day 5 after the addition of ropinirole, the ratio of CV caspase 3-positive neurons was measured in the same manner as in Example I-3.

Figure 15:
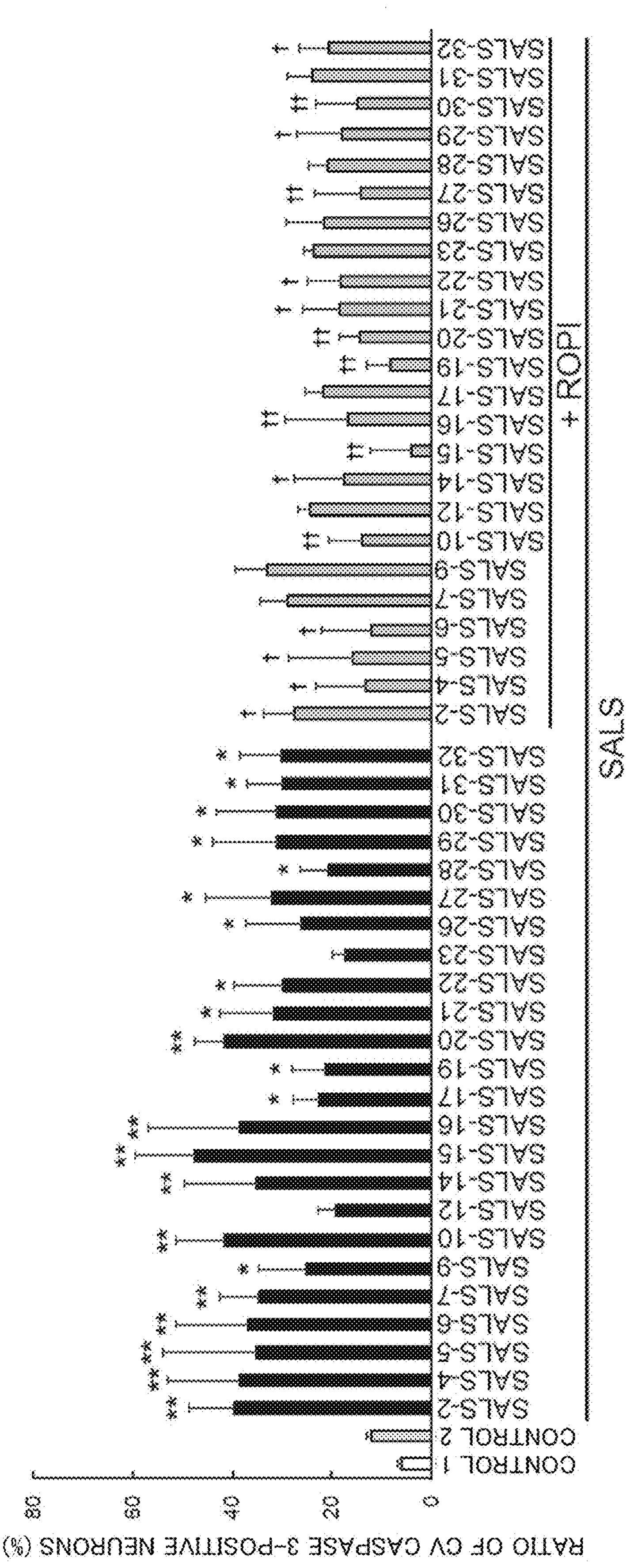
FIG. 15 is a graph showing the ratio of CV caspase 3-positive neurons in each motor neuron measured in Example III-5.

FIG. 15 is a graph showing the measurement results of the ratio of CV caspase 3-positive neurons. In the diagram, "**" and "++" indicate that there is a significant difference when the risk is less than 1%, and "+ROPI" represents the result of adding ropinirole to the medium. As a result, among the 24 SALS model cases, there were 22 cases in which an increase in the CV caspase 3-positive ratio was confirmed. In addition, among these 22 cases, there were 16 cases in which the increase in CV caspase 3-positive ratio was suppressed by the addition of ropinirole (72.73% of SALS cases).

This result further supports ropinirole being effective not only for familial ALS but also for sporadic ALS treatment.

INDUSTRIAL APPLICABILITY

According to the present invention, it is possible to provide a therapeutic agent for ALS and a composition for treatment of ALS. It is possible to treat not only familial ALS but also sporadic ALS with the therapeutic agent for ALS or composition for treatment of ALS of the present invention. In addition, it is possible to clarify the disease mechanism of ALS by analyzing the mechanism of action of the therapeutic agent for ALS of the present invention with respect to motor neurons differentiated from iPS cells derived from ALS patients.

The invention claimed is:

1. A method of treating sporadic amyotrophic lateral sclerosis (ALS), or familial ALS having a mutation in the FUS gene and/or TAR DNA-binding protein 43 kDa (TDP-43) gene, after onset of the ALS phenotype, comprising:

administering an effective amount of a compound represented by Formula (1), a pharmaceutically acceptable salt thereof, or a solvate thereof to a patient in need thereof

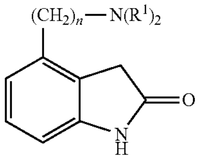

(1)

in Formula (1), $R^1$ each independently represents an alkyl group having 1 to 6 carbon atoms or a 4-hydroxyphenethyl group, and n represents an integer of 1 to 3.

2. The method according to claim 1, wherein n in Formula (1) is 2.

3. The method according to claim 1, wherein $R^1$ in Formula (1) is an n-propyl group.

4. The method according to claim 1, wherein the compound represented by Formula (1) is 4-(2-di-n-propylaminoethyl)-2 (3H)-indolone.

5. The method according to claim 1, wherein the pharmaceutically acceptable salt of the compound represented by Formula (1) is 4-(2-di-n-propylaminoethyl)-2 (3H)-indolone hydrochloride.

6. A method of treating sporadic ALS, or familial ALS having a mutation in the FUS gene and/or TDP-43 gene, after onset of the ALS phenotype, comprising:

administering an effective amount of a composition to a patient in need thereof, wherein the composition includes a compound represented by Formula (1), a pharmaceutically acceptable salt thereof, or a solvate thereof and a pharmaceutically acceptable carrier

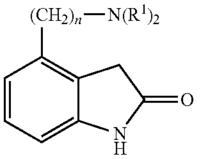

(1)

in Formula (1), $R^1$ each independently represents an alkyl group having 1 to 6 carbon atoms or a 4-hydroxyphenethyl group, and n represents an integer of 1 to 3.

* * * * *